US00PP09841P

United States Patent [19]

Edwards

[11] Patent Number: Plant 9,841

[45] Date of Patent: Apr. 1, 1997

[54] PEACH TREE NAMED 'EDWARDS AMBROSIA'

[76] Inventor: Mack H. Edwards, P.O. Box 469, Springville, Calif. 93265

[21] Appl. No.: 529,034

[22] Filed: Sep. 15, 1995

[51] Int. Cl.[6] ..... A01H 5/00

[52] U.S. Cl. ..... Plt./42.1

[58] Field of Search ..... Plt./42.1

[56] References Cited

PUBLICATIONS (Listing for) Ambrosia "Alphabetical Listing of Denominations", *Plant Patent Directory,* 1993 National Association of Plant Patent Owners p. 0002.

*Primary Examiner*—James R. Feyrer

[57] ABSTRACT

A new distinct variety of white peach with the following noted uniqueness:

1. A late maturing white peach of large size.
2. Fruit with excellent flavor, aroma, and eating quality.
3. Fruit with firm flesh and good shipping and storing qualities when handled carefully.
4. Fruit with bright attractive red and yellow skin color.
5. Fruit with very high soluble solids.
6. Fruit that can be eaten with skin on with no bitter after taste.
7. Fruit with very little skin pubescence.
8. A tree with very vigorous upright growth.
9. A tree that is early bearing.
10. A tree that is tolerant of peach leaf curl.
11. A white peach that maintains its flesh firmness, color, and flavor when canned or preserved.

4 Drawing Sheets

BACKGROUND OF THE VARIETY

This present invention relates to a new and distinct variety of peach tree discovered as a seedling and grown as a seedling, denominated 'Edwards Ambrosia' peach tree", broadly characterized by its large full freestone fruit of firm sweet white flesh with high soluble solids and more particularly to a fruit with a skin of attractive red and cream color, a skin that when the fruit is firm ripe is tenacious to the flesh and so nearly devoid of pubescence, the fruit may be eaten, skin and flesh, without tartness or bitter after taste. This premium white peach ripens during the last week in August in Springville, Tulare County, the San Joaquin Valley of California. The botanical classification of this tree is *Prunus persica.* In market class, this tree is a late bearing, white fleshed, freestone peach.

The commercial value of a quality white peach is dependent in large part to reaching a market when fewer peaches are available and particularly premium white peaches. As a comparison to 'Edwards Ambrosia' peach, three different varieties of white peach were purchased in local supermarkets on Sep. 3, 1995, the differences are noted below.

| Name | Avg. Weight | Skin Color | Skin Thick | Flesh Color | Pubescence Pubescence | Soluble Soluble Solids |
|---|---|---|---|---|---|---|
| Ito #4401 | .44 lbs | 2A3 | .0153 | 2A2 | light | 10.5 |
| 'Champagne' | .38 lbs | 2A3/ 9E8 | .0117 | 2A2 | Medium | 11.2 |
| 'Sept Snow' | .38 lbs | 2A3/ 9D7 | .0145 | 3A3 | Medium | 11.7 |
| 'Edwards Ambrosia' | .49 lbs | 4A4/ 9D7 | .0096 | 2A3 | very light | 15.5 |

Harvesting date of 'September Snow' is said to be from August 25 to September 8. Soluble solids tests were done by the Tulare County Agriculture Department. 'Edwards Ambrosia' soluble solids tests was witnesed by Joseph Tucker, 2500 Sophia Ln., Kingsburg, Calif. 93631.

Tree value is further enhanced by its late and short picking window from August 23 to September 1, allowing the fruit to be picked, packed, and shipped in a very short time. Shipping quality of this fruit is good in the tests made but it must be handled and packed carefully. This tree is very productive and its many showy blossoms could have some commercial value. Value is added also by the ability of this firm fleshed white fruit to maintain its shape and integrity under home canning methods.

ORIGIN OF THE VARIETY

This seedling tree is one of six seedlings that were found in our small orchard in Springville, Calif. in 1989. The seedlings were potted and encourgaged to grow; two of the six seedlings survived and were planted in the orchard in 1990, bore first fruit in 1992. One of the remaining trees is the subject of this disclosure. This fruit was so outstanding I named it 'Edwards Ambrosia' peach and was encouraged by the University of California Farm Advisor to apply for a patent. Parental generation of this tree and fruit is unknown.

ASEXUAL REPRODUCTION OF THE VARIETY

Asexual reproduction of 'Edwards Ambrosia' peach was accomplished, in the same orchard, by grafting scion wood from the original seedling to Nemaguard rootstock which produced a small tree that produced many fruit 22 months from the graft date, that fruit identical in every way to the original parent. Grafts to a Rio Oso Gem tree and on another seedlings peach tree produced fruit identical to the original parent. All grafts were cleft grafts.

SUMMARY OF THE VARIETY

This new variety of white peach is characterized by its late ripening date of approximately August 23, three weeks after the 'Elberta' peach and at about the same time as the patented peach 'September Snow' here in the ecological conditions prevailing in our orchard in Springville, Calif. 'Edwards Ambrosia' peach is larger than those being marketed at this time and appears to be more colorful. Ground color is yellow overlayed with red, colors usually equally spread. Fruit is full freestone of large size with excellent flavor and firm, juicy flesh very high in soluble solids, flesh that may be eaten with the skin on without bitterness. The skin has very little pubescence. Fruit stores well under refrigeration and ships well if hand picked and handled carefully. It is an excellent canning peach. The tree is of medium size, very vigorous and a heavy producer. The tree and its clones are very tolerant to peach leaf curl.

BRIEF DESCRIPTION OF THE VIEWS OF THE DRAWING

Sheet 1 shows three specimens of whole fruit at picking ripe, along the top, at different orientations; the one on the left showing the stem-end, the middle being in side-view and the one on the left showing the side with the shallow suture. Whole fruit ground color and the pattern, shade and character of the overcolor is depicted. Also depicted, on the lower left, is one fruit split on the suture plane with the stone removed and shown separately. Two leaves with the underside and top surface shown, respectively, are illustrated in the lower right of this sheet.

Sheet 2 is an enlarged view of the blossom showing the petal coloration and character, and the reproductive organs including the stamens with anthers, and the pistil and stigma.

In sheet 3, the top photograph shows the canopy density of a young specimen of the tree having a moderately spreading vase form. The bottom photograph illustrates an older specimen at a point approaching harvest; and showing the heavy productivity of this tree as it may affect the orientation of the bearing stems.

In sheet 4, the top photograph is a close-up of a single fruit on the tree. The bottom left photograph shows a stem, at fruiting wood stage, bearing a typical number of flowers. The bottom right photograph shows a single specimen of the tree at a commercial stage of maturity.

BOTANICAL DESCRIPTION OF THE TREE

The descriptions of the tree to follow were made of tree specimens growing under the ecological conditions prevailing in my orchard in Springville, Calif. It is to be understood that the phenotype of this tree may slightly vary under somewhat different conditions of culture. All color code identifications for the various plant parts have been made with reference to the *Reinhold Color Atlas* by A. Kornerup and J. H. Wanscher, except where ordinary color descriptions are clear and appropriate.

Tree:

a. *Size.*—Medium. (1) Pruned to 8' height 1995 season. (2) Height Sep. 1, 1995=14'. (3) Breadth Sep. 1, 1995=10'.
b. *Vigor.*—Vigorous. Tree is 5 years in orchard. (1) Terminal growth 1995 season to 6'. (2) Tree received no fertilizer of any kind 1995.
c. *Form.*—Upright — vase formed.
d. *Growth.*—Upright to spreading. (1) This tree is the original seedling.
e. *Density.*—Dense.
f. *Hardiness.*—Hardy. (1) Chilling hours 1995=805 hours. (2) Two dormant oil sprays applied 1995. (3) No other insecticide or disease applications 1995. (4) Tree and clones tolerant to peach leaf curl.
g. *Production.*—Heavy. (1) Tree blooms and sets fruit prodigiously. (2) Tree structure gives ample on tree storage for fruit. (3) Thinning of green fruit in spring is required.
h. *Bearing.*—Regular and heavy bearer. (1) Pollination: Tree is self pollinating.
i. *Trunk.*—Medium size. (1) Circumference 16" one foot above ground level. (2) Texture: Medium Rough. (3) Color: 8D2 Brownish Grey.
j. *Branches.*—(1) Size: Medium. (2) Texture: Rough. (3) Color: A. Terminal Growth: 1B6 Greenish Yellow. B. Young Branches: 8E4 Redish Brown. C. Mature Branches: 5C2 Brownish Gray. D. Lenticels: Approximately 6 to 8 per square inch.

Leaves:

a. *Size.*—Medium, average mature leaves 5½" to 8" long, width 1¾".
b. *Texture.*—Smooth.
c. *Petiole.*—Length ¾". Width ⅛", Color: 29A6 Greenish yellow.
d. *Leaf color.*—Dorsal — 28E8 Deep Green. Ventral side — 28D7 Green.
e. *Glands.*—2 to 3 opposite — shape reniform — medium size.
f. *Leaf shape.*—Lanceolate. Base truncate. Type reticulate. Margin: Serrate.

Flower buds.

a. *Hardiness.*—Known to 19 degrees F and heavy frost.
b. *Size.*—Medium to large, usually in twos, randomly in threes.
c. *Diameter.*—Approximately 11/16".
d. *Length.*—Average ⅜".
e. *Form.*—Plump.
f. *Pubescence.*—Pubescent.
g. *Abundance.*—Prodigious, 32 flower buds noted on 15" branch 1994.

Flowers:

a. *Shape.*—Actinomorphic. Symmetrical. 5 Petals.
b. *Size.*—Large and showy — Diameter 1½".
c. *First bloom.*—About Mar. 1, 1995.
d. *Pollen.*—Pollen present.
e. *Color.*—14A5 Purplish Pink.
f. *Pollination requirements.*—Self pollinating.

Fruit:

a. *Maturity when described.*—Firm Ripe, approximately August 23.
b. *Date of last picking.*—Sep. 1, 1995.
c. *Size.*—Large. Average diameter axially 2½" to 3".
d. *Form.*—Spherical.
e. *Suture.*—Shallow.
f. *Apex.*—Rounded to slightly retuse.
g. *Cavity.*—Elongated in suture plane. Average depth 7/16". Average breadth ⅝".
h. *Aroma.*—Very aromatic.
i. *Stem cavity depth.*—½" — Width to suture 1⅜".
j. Fruit hangs well on tree with no tendency to preharvest fruit drop.

Flesh:

a. *Ripening.*—Uniform.
b. *Texture.*—Firm.
c. *Fiber.*—Very little — tender.
d. *Juice.*—Very juicy.
e. *Flavor.*—Mild, sub acid, good balance between sugar/acid.
f. *Soluble solids.*—15.5
g. *Aroma.*—Aromatic.
h. *Eating quality.*—Excellent.
i. *Preserving quality.*—Good.
j. *Color.*—2A2 Yellowish White.
k. *Pit cavity color.*—11C7 Dark Red.

Skin:

a. *Thickness.*—0.0096".
b. *Texture.*—Smooth, tenacious to flesh.
c. Tendency to crack.—None.
d. *Pubescence.*—Very little.
e. *Color.*—Firm ripe — 1A6 Greenish Yellow Ground Color, 9D7 Brownish Red Overlay. Full ripe—4A4 Light Yellow, 9D7 Brownish Red.
f. Skin may be eaten with flesh, no bitter aftertaste.

Stone:

a. Freestone.
b. *Size.*—Average length 1½", Average width 1⅛", Average Thickness ⅝".
c. *Form.*—Ovid.
d. *Base.*—Rounded.
e. *Sides.*—Slightly rounded.
f. *Surface.*—Furrowed toward base, center and apex pitted, with furrow on outside edge from base to apex.
g. *Ridges.*—Rounded.
h. *Tendency to split.*—None.
i. *Color.*—7D5 Brown.

Use of fruit:

a. *Desert fruit.*—Soluble solids 15.5, very sweet with excellent flavor. Can be eaten with skin on with no bitter aftertaste.
b. *Market.*—Local and long distance.
c. *Shipping quality.*—Good, fruit must be picked, handled, and packed carefully.

d. *Marketing advantage.*—Large, attractively colored, aromatic peach with delicious flavor that will reach a late peach market.

I claim:

1. This is a new, and distinct variety of white fleshed peach tree, as described and illustrated, as grown under the ecological conditions prevailing near Springville, Tulare County, Calif., this peach is characterized by its late ripening time of approximately August 23, its tendency to bear on young trees, its ability to produce large sweet fruit every year, its high soluble solids and its nearly pubescence free skin; and, the tree has vigorous upright growth that is tolerant of peach leaf curl and produces large yellow and red attractive fruit.

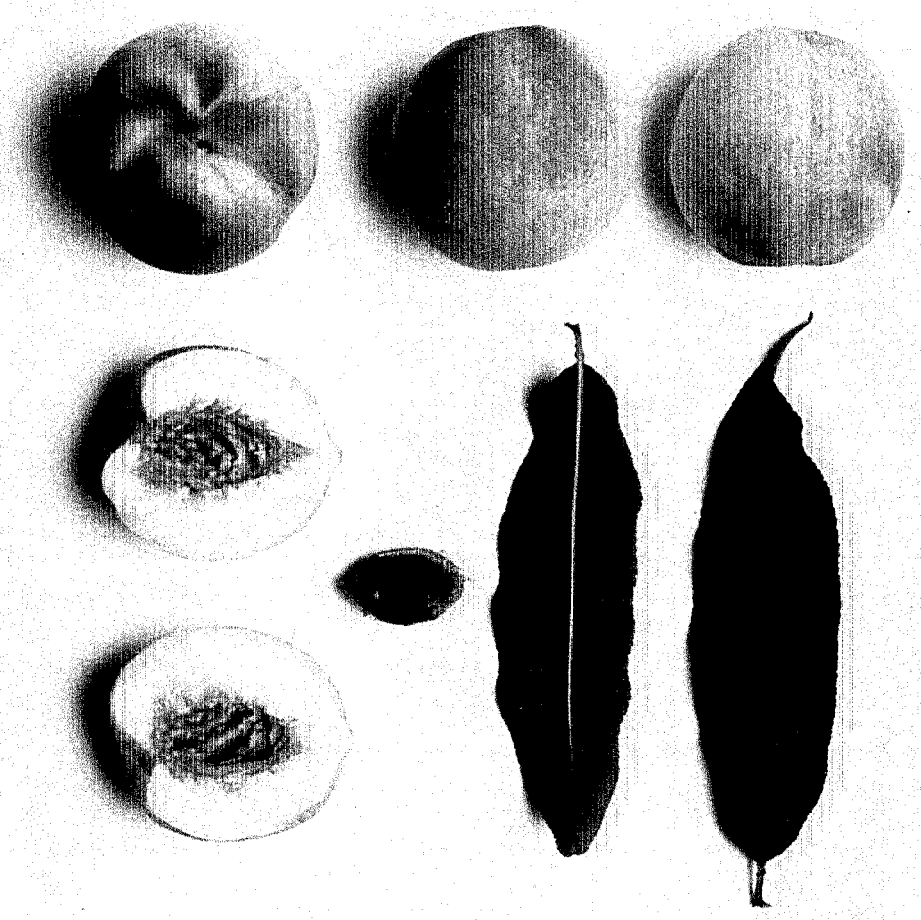

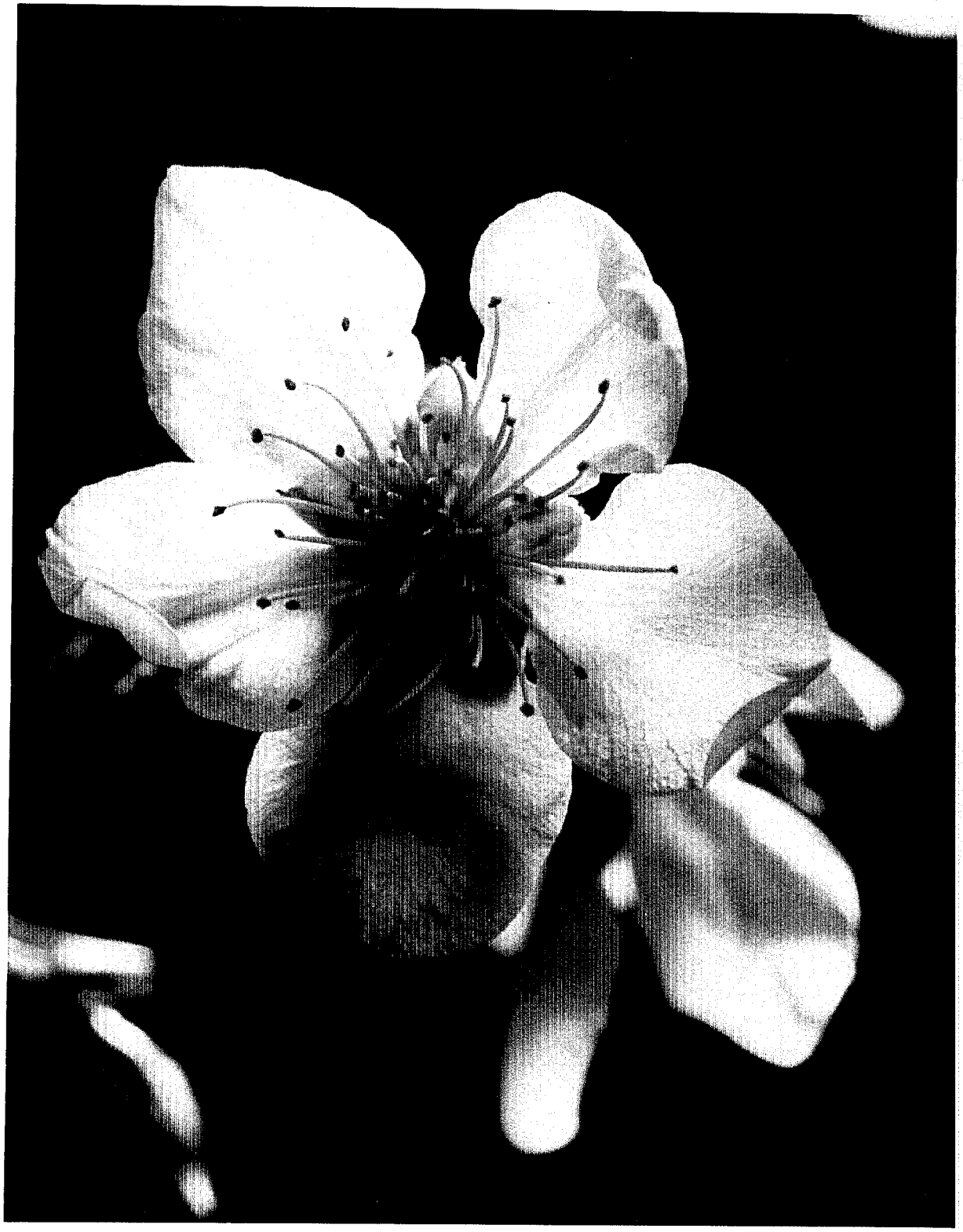

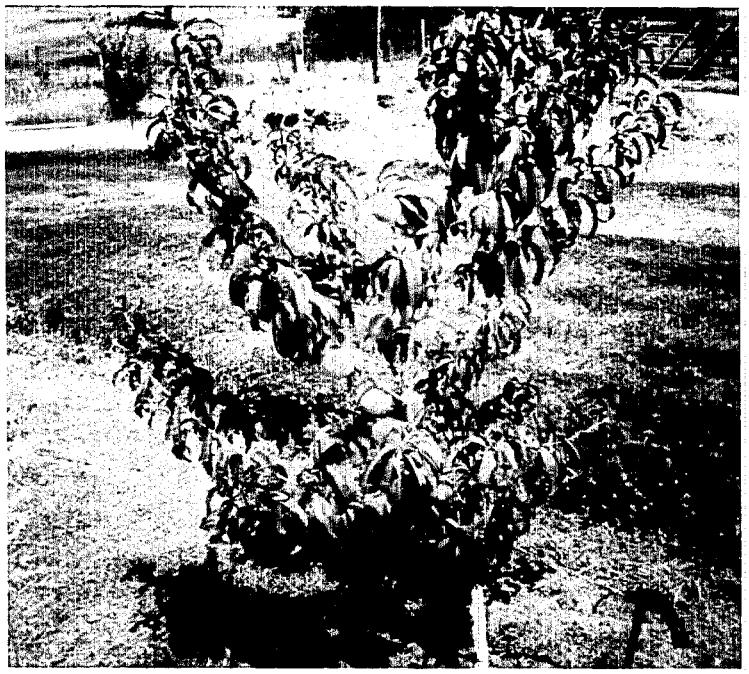
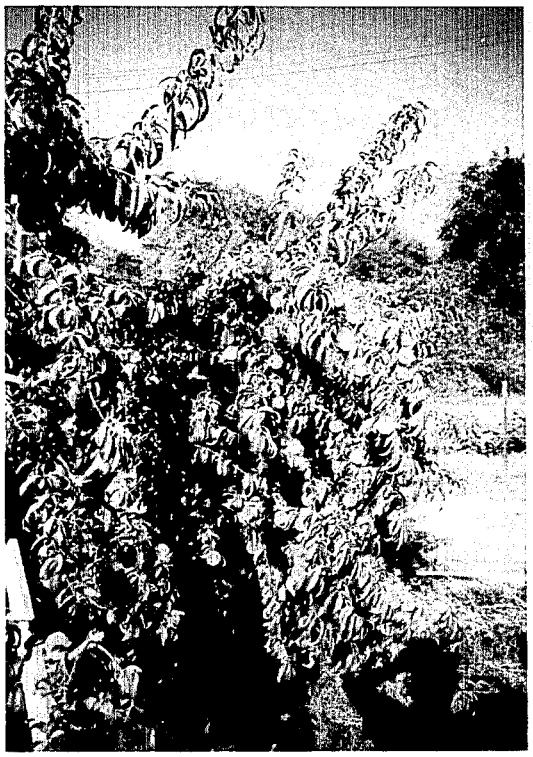

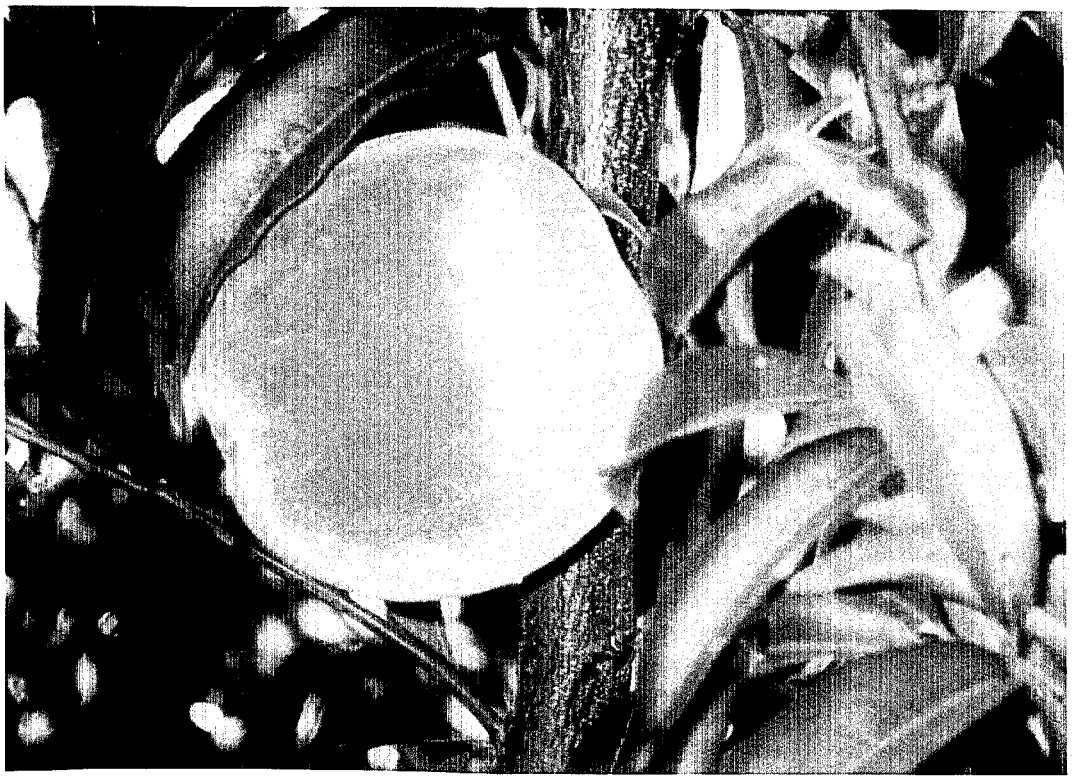
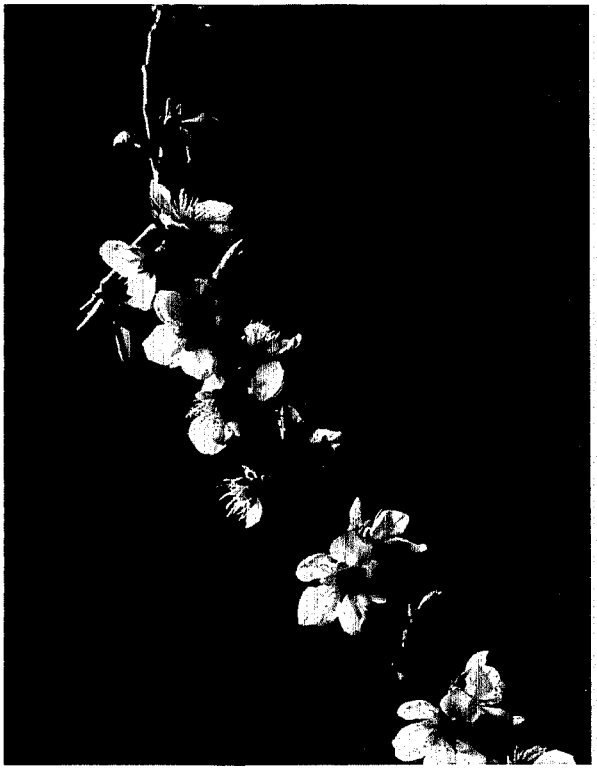
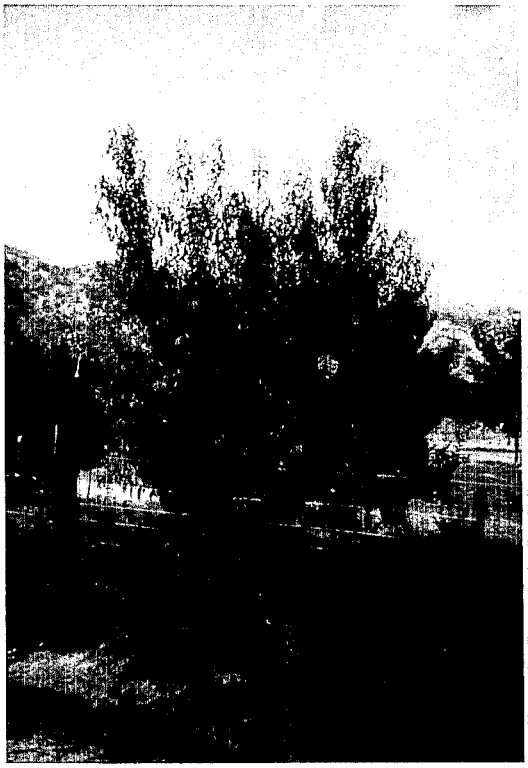

* * * * *